United States Patent [19]

Hall

[11] Patent Number: 5,540,088
[45] Date of Patent: Jul. 30, 1996

[54] RHEOMETER AND METHOD OF MEASURING RHEOLOGICAL PROPERTIES

[75] Inventor: Richard W. Hall, Cleethorps, England

[73] Assignee: Bohlin Instruments Limited, England

[21] Appl. No.: 184,994

[22] Filed: Jan. 24, 1994

[51] Int. Cl.[6] ............................. G01N 11/00; G01N 11/14
[52] U.S. Cl. ........................... 73/54.43; 73/54.28; 374/48
[58] Field of Search ............................. 73/54.43, 54.28; 374/48, 47

[56] References Cited

U.S. PATENT DOCUMENTS

| | | | |
|---|---|---|---|
| 1,652,525 | 12/1927 | Hahnemann et al. | 374/47 |
| 3,056,283 | 10/1962 | Tiede | 73/54.43 |
| 3,182,494 | 5/1965 | Beatty et al. | 374/48 |
| 3,531,996 | 10/1970 | Harris et al. | 374/48 |
| 4,472,963 | 9/1984 | Gyer et al. | 73/54.43 |
| 4,643,021 | 2/1987 | Mattout | 73/54.28 |
| 4,878,379 | 11/1989 | Deer | 73/54.43 |

FOREIGN PATENT DOCUMENTS

| | | | |
|---|---|---|---|
| 0156835 | 12/1980 | Japan | 374/47 |
| 40658863 | 3/1994 | Japan | 73/54.43 |
| 0586369 | 12/1977 | U.S.S.R. | 73/54.28 |
| 1518724 | 10/1989 | U.S.S.R. | 73/54.28 |

Primary Examiner—Diego F. F. Gutierrez
Attorney, Agent, or Firm—Kinney & Lange

[57] ABSTRACT

A rheometer has temperature control means which include a bath through which liquid is circulated, so that it will completely immerse both the upper and lower probes or plates between which a sample, whose rheological are being investigated, is located. This allows the temperature of the sample to be closely controlled to within 0.2° C. of a selected temperature. The rheometer is particularly suitable for measuring the properties of bitumous materials which are extremely temperature sensitive.

19 Claims, 3 Drawing Sheets

RHEOMETER AND METHOD OF MEASURING RHEOLOGICAL PROPERTIES

BACKGROUND OF THE INVENTION

This invention relates to a rheometer and to a method of measuring the rheological properties of a sample, particularly a sample of bitumous material.

Rheometers are well known instruments for measuring the rheological properties of samples, normally placed between the facing surfaces of upper and lower probes or plates one of which is driven relative to the other. The rheometer includes measuring means, such as strain gauges and position gauges for measuring the movement strains induced between the probes in accordance with the properties of the sample. The rheometer is connected to computer means for analysing these measurements so that a computerised control functions to enable the rapid determination of the tested materials properties over a broad range of possible testing frequencies and temperatures. The operating software allows the rheometer to be programmed easily for different test procedures.

Measurable visco-elastic parameters include the modulus, which is the ratio of the applied torque to resultant strain, and the phase angle, which is defined as the phase shift between the stress and strain waves. Presentation of other related visco-elastic parameters such as storage and loss modulus is also possible.

PRIOR ART

It is known for rheometers to include some form of temperature control because the visco-elastic properties are temperature dependent. However, known temperature controls consist either of immersing the lower surface of the lower plate in a water bath without controlling the temperature of the upper plate, or of circulating a gas around both the upper and lower plates.

SUMMARY OF THE INVENTION

An object of the present invention is to provide an improved temperature control means in a rheometer.

Bitumous materials, for example asphalt cements, commonly used in forming paving (road surfaces) are extremely temperature sensitive. For example, the visco-elastic parameters can vary by as much as 20% for 1° C. variation in temperature. For measuring the visco-elastic parameters of such materials a much closer temperature control than that known in present rheometers is desirable. A further object of the invention is to provide a rheometer in which the temperature of the sample can be controlled during measurement to within 0.2° C. of a selected temperature, preferably to within ±0.1° C. of the selected temperature, over the entire working range (preferably 5 to 90° C.) of the apparatus.

Accordingly, in one aspect, the invention provides a rheometer comprising an upper probe and a lower probe having facing surfaces for receiving between them a sample whose rheological properties are to be investigated, mounting means mounting the upper and lower probes so that they can be brought adjacent one another and the upper probe can be rotated, drive means for causing rotational movement of the upper probe relative to the lower probe, measuring means for measuring the visco-elastic properties of a sample located between said surfaces during such relative movement, means for circulating liquid around both the upper and lower probes and any sample located therebetween, and means for controlling the temperature of the liquid at a selected temperature.

With such an arrangement the temperature of both probes (preferably in the form of plates) and the sample can be carefully controlled so that consistent and meaningful measurements can be made, even of bitumous samples. The means for controlling the temperature preferably controls the temperature to within 0.2° C., with advantage within 0.1° C.

Preferably the means for controlling the temperature allow a temperature to be selected anywhere within the range 5 to 90° C. In this case the liquid is normally water provided that this is immiscible with the sample.

The temperature range can be extended by using other liquids provided these are immiscible with the sample, for example with bitumous samples ethanol at lower temperatures and silicon oil at higher temperatures.

Preferably the means for circulating liquid includes a bath for containing liquid, the bath having a base, bath side walls and a substantially open top, and means for circulating liquid through the bath and over the side walls. The lower probe comprises a plate having an upper surface to receive the sample and a lower surface mounted at the top of the bath so that the liquid circulating therein will contact the lower surface of the plate. A bath cover having cover side walls is locatable over the bath so as to form an upward extension of the bath side walls to prevent liquid flowing over the bath side walls, the cover having liquid outlet means at a height greater than the upper surface of the upper probe in use, such that when the cover is in said position on the bath the upper and lower probes and any sample between their facing surfaces will be immersed in the liquid.

With this arrangement the bath without the cover can be used to control the temperature of the lower surface of the lower probe or plate so that the rheometer can be used with a sample out of contact with any liquid. However when the cover is located on the bath the temperature of the upper probe or plate together with the sample is also closely directly controlled.

The cover may be formed in two parts.

In another aspect the invention provides in a method of measuring the rheological properties of a sample of bitumous material located between the upper and lower probes of a rheometer, the step of immersing the sample and the upper and lower probes during measurement in a liquid and controlling the temperature of the liquid to within 0.2° C. of a selected temperature such that the temperature of the sample is also within 0.2° C. of the selected temperature, and preferably within 0.1° C. of that selected temperature.

Preferably the liquid is water.

BRIEF DESCRIPTION OF THE DRAWINGS

One embodiment of rheometer, in accordance with the invention, will now be described, by way of example only, with reference to the accompanying drawings of which.

DETAILED DESCRIPTION OF ONE EMBODIMENT

Figure 1:
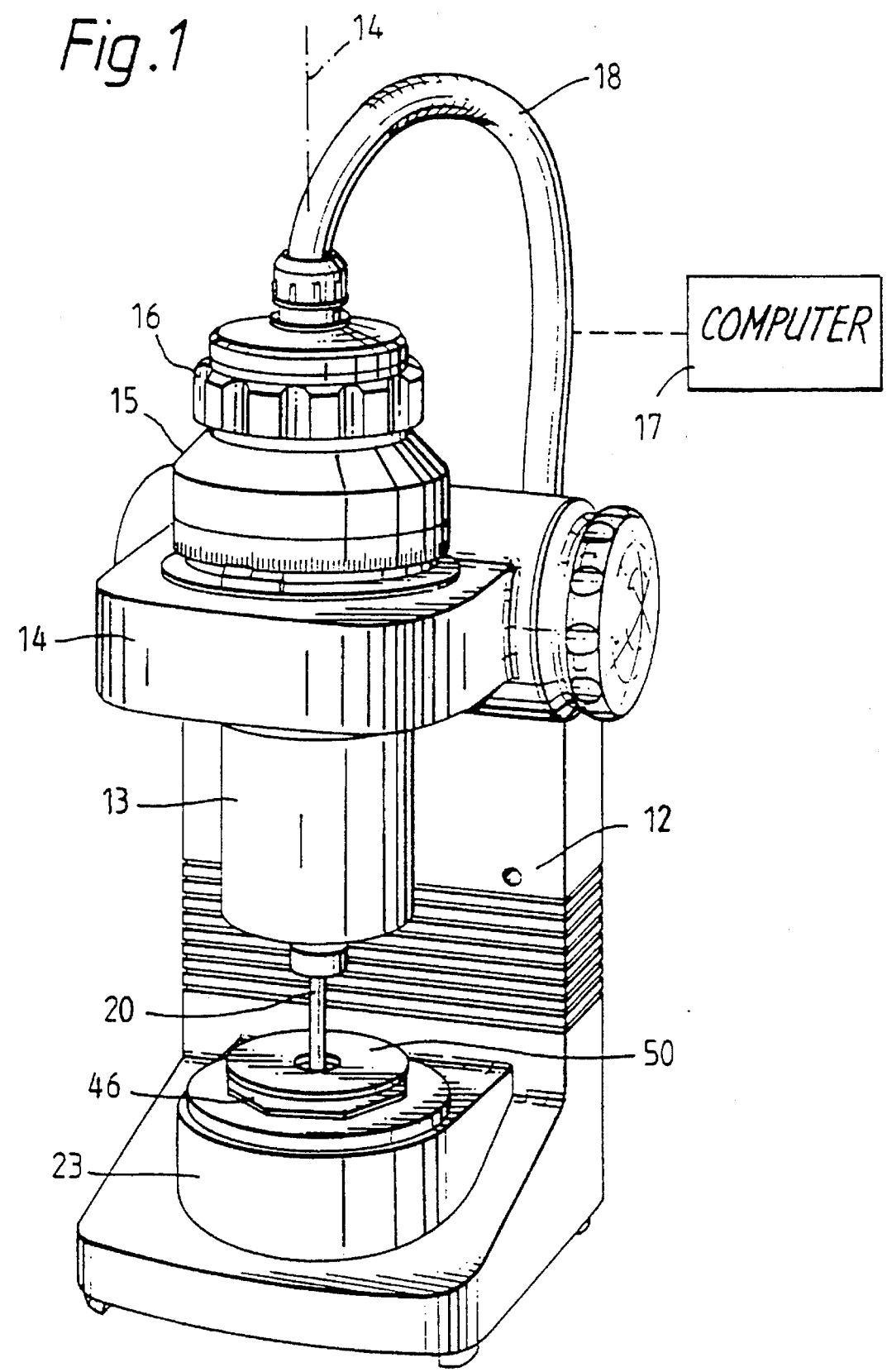
FIG. 1 is a general perspective view of a rheometer.
Figure 2:
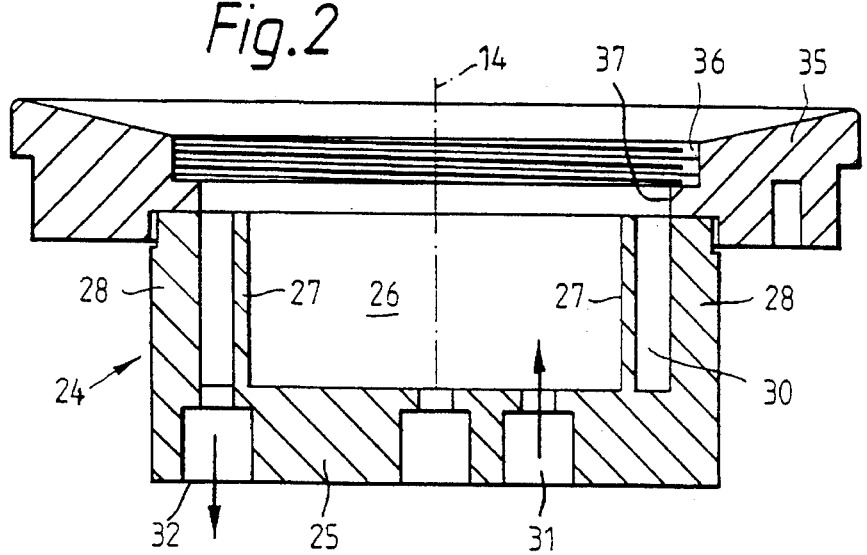
FIG. 2 is a sectional view of water bath of the rheometer.

The rheometer of FIG. 1 is of known form, apart from the temperature controlling means, and will not be described in detail. The rheometer comprises a rigid frame 12 in which a measuring spindle 13 is mounted in an air bearing so that it can be rotationally oscillated about its vertical axis 14 by a drive motor 15. Adjustment means 16 allows adjustment of the height of the spindle, and air and electrical connections to a computer 17 are supplied through a pipe 18. The measuring spindle carries an upper plate 19 (best seen in FIGS. 5 and 6) having a connecting spindle 20, an upper surface 21 and a lower horizontal surface 22. In some cases this lower surface will be slightly conical. The lower horizontally extending part 23 of the frame 12 houses a water bath 24 and a lower plate member 40 best seen in FIGS. 2 and 3.

The bath comprises a container having a base 25, a central compartment 26 for containing liquid defined by annular side wall 27 and having an open top. Outer annular support wall 28 is spaced from the wall 27 to define an annular space 30. The base defines a liquid inlet 31 and the annular space 30 is connected a liquid outlet 32. The inlet and outlet are connected to a water supply 29 including pump circulating means 33 and a temperature control mechanism 34, indicated diagrammatically in FIG. 6.

Located on top of the support wall 28 is an annulus 35 defining an internally threaded bore 36 and a counter bore 37 of the same dimension as the outer dimension of the annular channel 30.

Figure 3:
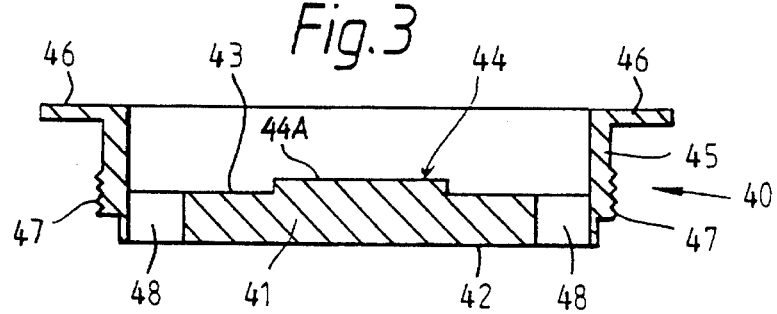
FIG. 3 is a sectional view of the lower plate of the rheometer.
Figure 4:
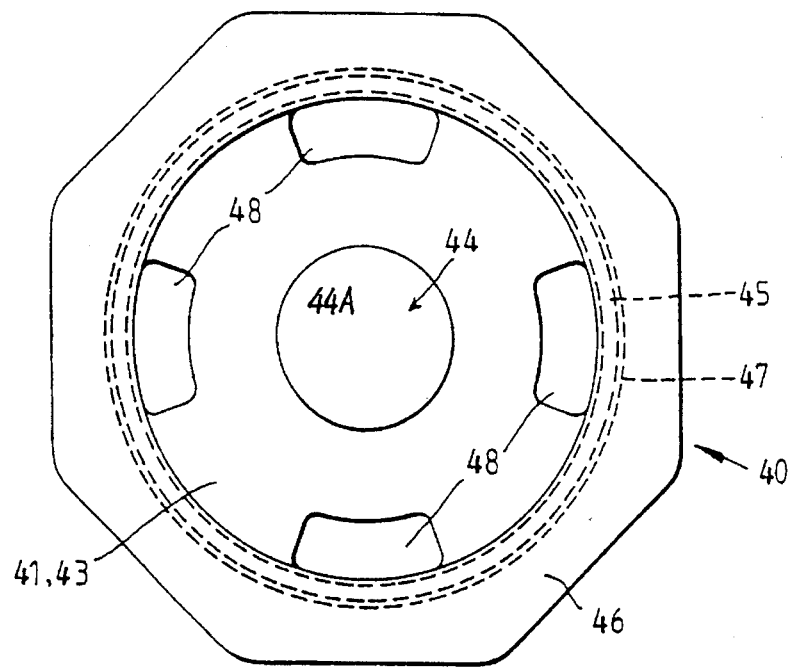
FIG. 4 is a plan view of the lower plate of the rheometer.

The lower plate member 40 of the rheometer, best seen in FIGS. 3 and 4, is designed to fit within the annulus 35. The lower plate member comprises a horizontally extending circular plate 41 having a flat lower surface 42, an upper surface 43 with a raised, flat, horizontal, circular central portion 44 having an upper, flat horizontal surface 44A, and upwardly extending annular side walls 45 ending in an outwardly projecting lip 46. Walls 45 are formed with an external screw thread 47 designed to mate with the thread 36. Four apertures 48 are formed in the plate 41 angularly spaced from one another adjacent the edge of the plate. When the plate member 40 is inserted in the bore 37 in annular member 35, with the threads 36, 47 tightly screwed together, the base of the plate 41 engages the tops of the walls 27 except in the areas of the apertures 48, and the lower surface 42 will be in contact with liquid in the bath compartment 26.

Figure 6:
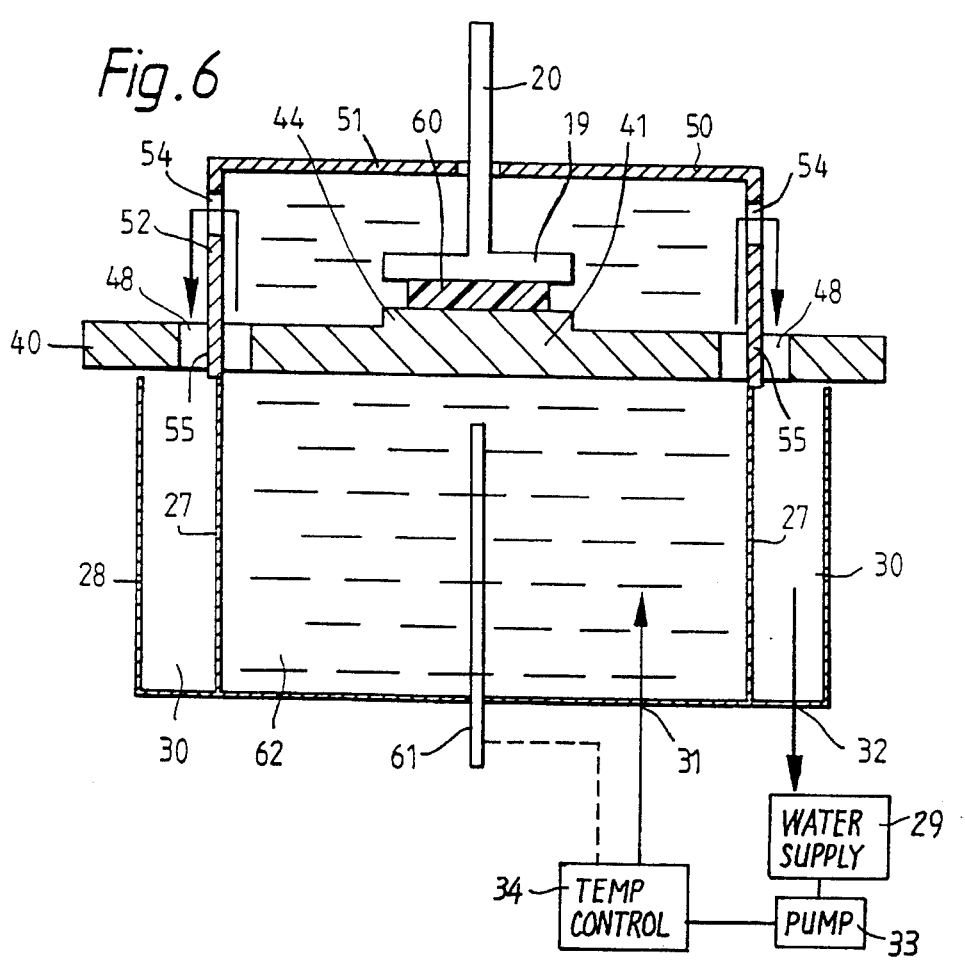
FIG. 6 is a view similar to that of FIG. 5 but showing the changed circulation of liquid when a cover member for the water bath is present.

As seen in FIG. 6, a removable cover member 50 is provided which can be placed over the bath and lower plate 41. The cover member has a top 51 with a central aperture to receive the spindle 20, and a downwardly projecting annular side wall 52 formed with apertures 54 angularly spaced from one another adjacent the top of the side wall. The side wall 52 is dimensioned to form a continuation of the side wall 27 of the water bath, and has four downwardly projecting feet 55 to extend into and effectively close off the top of the wall 27 in the areas of the apertures.

Figure 5:
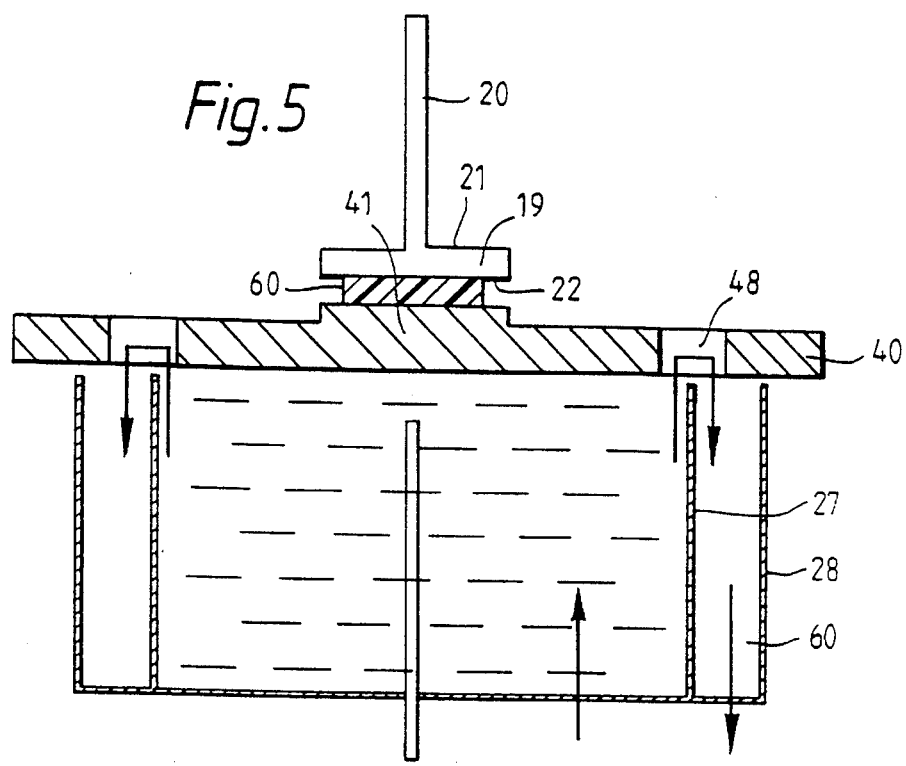
FIG. 5 is a diagrammatic view of the water bath lower plate and an upper plate showing how water circulates therein when no cover member is present.

In use a sample to be measured is placed between the facing surfaces 22, 44A of the upper and lower plates as seen at 60. A known platinum resistance thermometer 61 is located in the water bath immediately below the lower plate 41; water 62 at a selected temperature, controlled by the thermometer 61 and temperature control means 34 of known form to within 0.1° C. of the selected temperature, is pumped into the water bath. As seen in FIG. 5, when the cover member is not present, the water flows over the tops of the side walls 27 through the apertures 48 in the lower plate so that the lower surface 42 of the lower plate 41 is always in good contact with the flowing water. As seen in FIG. 6 when the cover member is placed over the water bath and upper and lower plates it effectively forms an upward extension of the side walls 27 so that the water level rises to the level of the apertures 54 in the cover plate. With this arrangement the whole of the lower plate, the whole of the upper plate and the sample are completely immersed in the liquid and therefore the temperature of the sample is closely maintained within 0.1° C. of the selected temperature. The rapid rate of heat transfer associated with a liquid heat exchange medium also minimises the time required to reach thermal equilibrium of the test sample.

Where the sample is a bituminous material it is preferred to use plates with flat parallel facing surfaces as the probes but it should be appreciated that other shapes are possible.

While the invention has been herein shown and described in what is presently conceived to be the most practical and preferred embodiment thereof, many modifications may be made thereof within the scope of the invention, which scope is to be accorded the broadest interpretation of the appended claims so as to encompass all equivalent structures and methods.

What is claimed is:

1. A rheometer comprising:

an upper probe and a lower probe having facing surfaces for receiving between them a sample whose rheological properties are to be investigated;

mounting means mounting the upper and lower probes so that they can be brought adjacent one another and relatively rotated;

drive means for causing such relative rotational movement of the probes;

measuring means for measuring the visco-elastic properties of a sample located between said surfaces during such relative movement;

means for circulating liquid around and in contact with both the upper and lower probes and any sample located therebetween; and means for controlling the temperature of the liquid at a selected temperature.

2. A rheometer according to claim 1 in which the means for controlling the temperature are arranged to control the temperature to within 0.2° C. of a selected temperature.

3. A rheometer according to claim 1 in which the means for controlling the temperature are arranged to control the temperature to within 0.1° C. of a selected temperature.

4. A rheometer according to claim 1 in which the means for controlling the temperature are arranged to control the temperature to any selected temperature in the range of 5° to 90° C.

5. A rheometer according to claim 1 in which the means for controlling the temperature include a thermometer and means mounting the thermometer directly beneath the lower probe.

6. A rheometer according to claim 1 in which the probes are plates and the facing surfaces are substantially horizontal.

7. A rheometer according to claim 1 in which the means for circulating liquid includes a bath for containing the liquid, the bath including a lower bath part having a base, lower bath side walls and a substantially open top, and means for circulating the liquid through the lower bath part and over the lower bath side walls; the bath including a removable bath cover having cover walls which are capable of being located over the lower bath part to form an upward extension of the lower bath side walls to prevent liquid flowing over the lower bath side walls, the cover having liquid outlet means at a height greater than the upper surface of the upper probe in use, such that when the cover is in said position on the lower bath part, the upper and lower probes and any sample between the facing surfaces thereof are immersed in the liquid.

8. A rheometer according to claim 7 wherein the lower probe comprises a lower plate having an upper surface to receive the sample and a lower surface mounted to the top of the lower bath part so that the liquid circulating therein contacts the lower surface of the plate.

9. A rheometer according to claim 8 in which the lower plate is located directly on the lower bath side walls and defines apertures aligned with the lower bath side walls so that any liquid flowing over the side walls passes through the apertures.

10. A rheometer according to claim 9 in which the bath cover has feet extending into the apertures to contact the lower bath side walls.

11. A rheometer according to claim 8 in which the lower plate has an external screw thread adapted to mate with an internal screw thread at the top of the lower bath part.

12. In a method of measuring the rheological properties of a sample of material located between an upper probe and a lower probe of a rheometer, the improvement comprising the steps of immersing the sample and the upper and lower probes during measurement in a liquid and controlling the temperature of the liquid to a selected temperature.

13. A method according to claim 12 in which the temperature of the liquid is controlled to within 0.2° C. of the selected temperature.

14. A method according to claim 12 in which the temperature is controlled to within 0.1° C. of the selected temperature.

15. A method according to claim 12 in which the liquid is water.

16. A method according to claim 12 in which the material is a bitumous material.

17. A rheometer for investigating rheological properties of a sample, the rheometer comprising:

an upper probe and a lower probe having facing surfaces for receiving the sample therebetween;

mounting means mounting the upper and lower probes so that they can be brought adjacent one another and relatively rotated;

drive means for causing such relative rotational movement of the probes;

measuring means for measuring the visco-elastic properties of a sample located between said surfaces during such relative movement;

a bath for containing the sample located between said surfaces;

means for circulating liquid in the bath;

first liquid level control means for maintaining the level of circulating liquid in the bath at a first level below the sample but in contact with the lower probe;

second liquid level control means for disabling the first liquid level control means and for maintaining the level of circulating liquid in the bath at a second level in which the liquid circulates around and in contact with both the upper and lower probes and the sample located therebetween; and means for controlling the temperature of the liquid at a selected temperature.

18. A rheometer according to claim 17 in which the bath is open to atmospheric pressure and in which the second liquid level control means comprise apertures in upright side walls of the bath.

19. A rheometer for investigating rheological properties of a sample, the rheometer comprising:

an upper probe and a lower probe having facing surfaces for receiving the sample therebetween, the upper and lower probes being positionable adjacent one another and rotatable relative to one another;

measuring means for measuring the visco-elastic properties of the sample located between said facing surfaces during relative rotational movement of the upper and lower probes;

a circulating liquid bath which maintains the circulating liquid at a first level below the sample but in contact with the lower probe; and liquid level control means for alternatively maintaining the level of the circulating liquid in the bath at a second level in which the liquid circulates around and in contact with both the upper and lower probes and the sample located therebetween.

\* \* \* \* \*

UNITED STATES PATENT AND TRADEMARK OFFICE
Certificate

Patent No. 5,540,088                                             Patented: July 30, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Richard W. Hall, Cleethorps, England; and Spencer M. Lovette, Katonah, NY.

Signed and Sealed this Twenty-first Day of February 2006.

DIEGO F. F. GUTIERREZ
*Supervisory Patent Examiner*
Art Unit 2859